United States Patent [19]
Chuang et al.

[11] Patent Number: 6,050,702
[45] Date of Patent: Apr. 18, 2000

[54] APPARATUS AND METHOD TO PROVIDE CUSTOM LIGHTING

[75] Inventors: Ping Derg Chuang; Choon Leong Ho; Wee Lee Sim; Michael Seet, all of Singapore, Singapore

[73] Assignee: Rahmonic Resources Pte. Ltd., Singapore, Singapore

[21] Appl. No.: 09/063,691

[22] Filed: Apr. 21, 1998

[51] Int. Cl.⁷ ..................................................... F21V 21/00
[52] U.S. Cl. ............................................ 362/249; 362/800
[58] Field of Search .................................... 362/249, 238, 362/239, 250, 251, 285, 418, 800, 252, 253, 234, 806, 103

[56] References Cited

U.S. PATENT DOCUMENTS

| | | | |
|---|---|---|---|
| 3,737,647 | 6/1973 | Gomi | 362/104 |
| 4,761,720 | 8/1988 | Solow | 362/249 |
| 5,155,669 | 10/1992 | Yamuro | 362/249 |
| 5,162,696 | 11/1992 | Goodrich | 362/800 |
| 5,580,163 | 12/1996 | Johnson, II | 362/285 |
| 5,769,533 | 6/1998 | Yamuro | 362/249 |
| 5,835,269 | 11/1998 | Natori | 359/448 |
| 5,895,115 | 4/1999 | Parker | 362/31 |

*Primary Examiner*—Sandra O'Shea
*Assistant Examiner*—Hargobind Sawhney
*Attorney, Agent, or Firm*—Fliesler Dubb Meyer & Lovejoy LLP

[57] ABSTRACT

A pliable light-emitting sheet consisting of a pliable sheet member provided with a plurality of light emitting elements. The light-emitting elements may consist of a densely arranged matrix of light emitting diodes. The sheet member is able to be pliably and curvaceously formed in a predetermined disposition or shape, and functions as a substantially continuous sheetlike light source. The pliable light-emitting sheet so formed is utilized to provide shadowless lighting for an object having features similar to the predetermined disposition or shape. The light emitting diodes may also be adjusted to provide light in a pattern to provide directional lighting so as to intentionally create a shadow on a protuberance or feature on an object.

23 Claims, 6 Drawing Sheets

APPARATUS AND METHOD TO PROVIDE CUSTOM LIGHTING

BACKGROUND OF THE INVENTION

1. Field of the Invention

The present invention relates to apparatus which are used to provide custom lighting. The present invention also relates to provision of shadowless lighting on an object, and a method of providing such shadowless lighting. The present invention also relates to providing shadowless light to objects of unusual shape, or having any one of crevices or interior surfaces.

The present invention also relates to provision of custom lighting that intentionally casts shadows about protuberances or other features of an object via directional lighting. The present invention is particularly related, but not exclusively, to the electronics manufacturing industry where electronics components and devices, for example, must be examined in either shadowless light or light that intentionally casts shadows, for instance, for quality control or inspection purposes.

2. Discussion of the Background

In the field of electronics manufacturing, it is often necessary to inspect a component visually under shadowless lighting conditions, so that every aspect and part of the surface topography of the component may be inspected for any surface defects.

There are known apparatus which are used for providing shadowless lighting, an example of which is U.S. Pat. No. 5,580,163 (Johnson). In this and other earlier patents, the ability to adjust various light elements is provided in the form of a mechanical apparatus that guides the lighting elements along predefined paths with respect to an object to be lighted. While the lighting elements in the prior art are moveable, such movement is constrained by the predefined mechanical guides.

Thus, these earlier apparatus are capable of providing shadowless lighting, but only when the object to be illuminated is of appropriate size and shape to be placed within the focus of these lighting elements. Such lighting apparatus are not able to readily accommodate irregular-shaped objects, or objects that do not conform to a light-receiving area of the apparatus. For example, the apparatus in the Johnson patent has a light-receiving area that is defined by a circular arrangement of lighting elements. Hence, the Johnson apparatus would not be readily adapted to provide lighting for a very long article that has dimensions which exceed the limited dimensions of the light-receiving area.

Figure 2A:
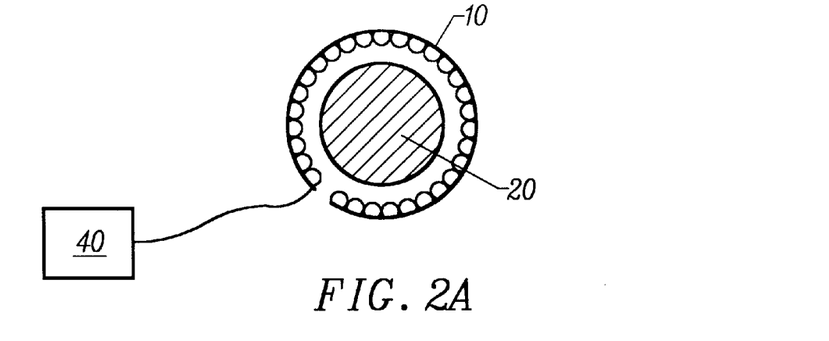
FIG. 2A is a cross sectional view of the perspective illustration of FIG. 1.
Figure 2B:
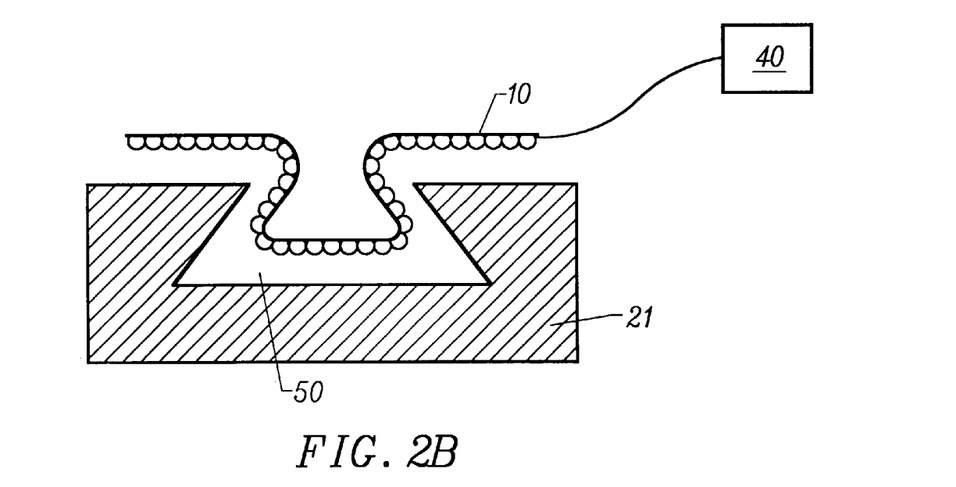
FIG. 2B is a cross sectional view of the present invention formed to provide shadowless lighting in a wedge-shaped cavity of an object.

Examples of irregular shaped objects are those objects that would not receive shadowless lighting, if the lighting elements merely surround the periphery of the object, perhaps because of irregular contours on the surface of the object. For example, the object in FIG. 2B is unlikely to receive shadowless lighting if the lighting elements merely surrounded the periphery of the object as a whole, without taking into account the cavity 50. Regular geometric objects would not have this problem, but manufactured products commonly have irregularly shaped portions, for example overhangs, projections, or cavities.

Another problem with lighting apparatus in which the lighting elements have a restricted range of movement, is that such apparatus cannot usually be used readily to light internal crevices or surfaces. For example, an inside of a cylinder would not be well lighted because of shadows cast by lighting not directed to a surface on the inside of the cylinder.

Another known method of providing shadowless lighting is to create the lighting source from a bundle of fiber optics. The individual fiber optics are tied or bundled together so as to surround the object. Where necessary, the bundle of fibers may be shaped by cutting the ends of the fibers. This method of creating shadowless lighting is flexible because the lighting apparatus is fashioned from individual fibers, which provides great flexibility in the variety of objects that can be lighted. However, since a bundle of fibers must be created specifically for each object to be lighted, this approach to providing shadowless lighting tends to be expensive.

Furthermore, a lighting device created by using fibers cannot be readily adapted for lighting further objects that are shaped differently to the object for which the bundle of fibers was prepared for initially. There is no flexibility in being able to re-use such apparatus, unless the further objects to be lighted are of similar size and shape to the original object. Finally, it is difficult to use optical fibers to create a lighting apparatus that can illuminate internal surfaces or crevices.

SUMMARY OF INVENTION

Accordingly, it is an object of the present invention to overcome or substantially ameliorate at least some of the problems found in the above-mentioned prior art by providing an illumination source capable of providing shadowless light on to surfaces of irregularly shaped objects that may include any number of overhangs, projections, cavities, or other surface anomalies.

It is another object of the present invention to provide a shadowless light source capable of readily lighting internal surfaces or crevices.

It is another object of the present invention to provide a custom light source able to cast shadows about protuberances or other features, thereby making the protuberance or feature readily identifiable.

These and other objects are accomplished by the present invention, which provides a light-emitting sheet that comprises a pliable and supple sheet member. The sheet member is provided with a plurality of light-emitting elements which are attached to the sheet member such that the sheet member is able to function as a substantially continuous sheet-like light source. Each of the light emitting elements are connectable to an electrical source. The supple sheet member is capable of being pliably and curvaceously shaped, i.e., bent at angles or shaped into curves, in order to allow the lighting sheet to conform to a desired disposition, curvature, or shape so that the light-emitting sheet is able to act as a shadowless light source for an object.

In one embodiment, each of the light emitting elements is a light emitting diode. Each of the diodes may be connected in parallel to the electrical source.

The plurality of elements are preferably supported on the sheet member as a densely arranged matrix of diodes. The pliable sheet member may be constructed of a pliable and supple printed circuit board (P.C.B.).

The object to be lighted may be irregularly shaped and, in such cases, the sheet member is capable of being formed into an irregular shape in order to substantially conform to the shape of the irregularly-shaped object so as to act as a shadowless light source.

Preferably, the supple sheet member is able to be set permanently in the desired disposition, curvature or shape using a reinforcing agent. The reinforcing agent may be an fiberglass-reinforced epoxy that is able to be applied to the surface of the sheet member.

Preferably, the intensity of light emitted from the plurality of light emitting elements is adjustable. The intensity of light emitted from at least one of the plurality of light emitting elements may be adjustable independently with respect to the light intensity of other of the plurality of light emitting elements.

In another embodiment, the plurality of light emitting elements are adjusted in intensity, turned on, and/or turned off at specific locations in order to intentionally cast shadows on or around a protuberance or feature of an object.

According to another aspect of the present invention, there is also provided a method of providing shadowless lighting on an object. The method comprises the steps of providing a pliable and supple sheet member with a plurality of light emitting elements which are attached to the sheet member such that the sheet member functions as a substantially continuous sheet-like light source, and pliably and curvaceously forming the pliable sheet member in at least one of a predetermined disposition, curvature, and shape in order to enable the light emitting elements to provide shadowless lighting on the object.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

The above-described figures have not been drawn to scale. Specifically, in FIGS. 1, 2 and 3, the lighting elements, in the form of L.E.D.s, have been drawn roughly for the sake of illustration, since the elements would otherwise not have been individually discernible if drawn to exact scale. Furthermore, the light-emitting sheet of the present invention would often be utilized to completely surround the illuminated object. However, in the diagrams, the sheets have not been illustrated as completely surrounding the object, in order to clearly indicate the sheet-like nature of the embodiments.

DESCRIPTION OF THE PREFERRED EMBODIMENTS

Figure 1:
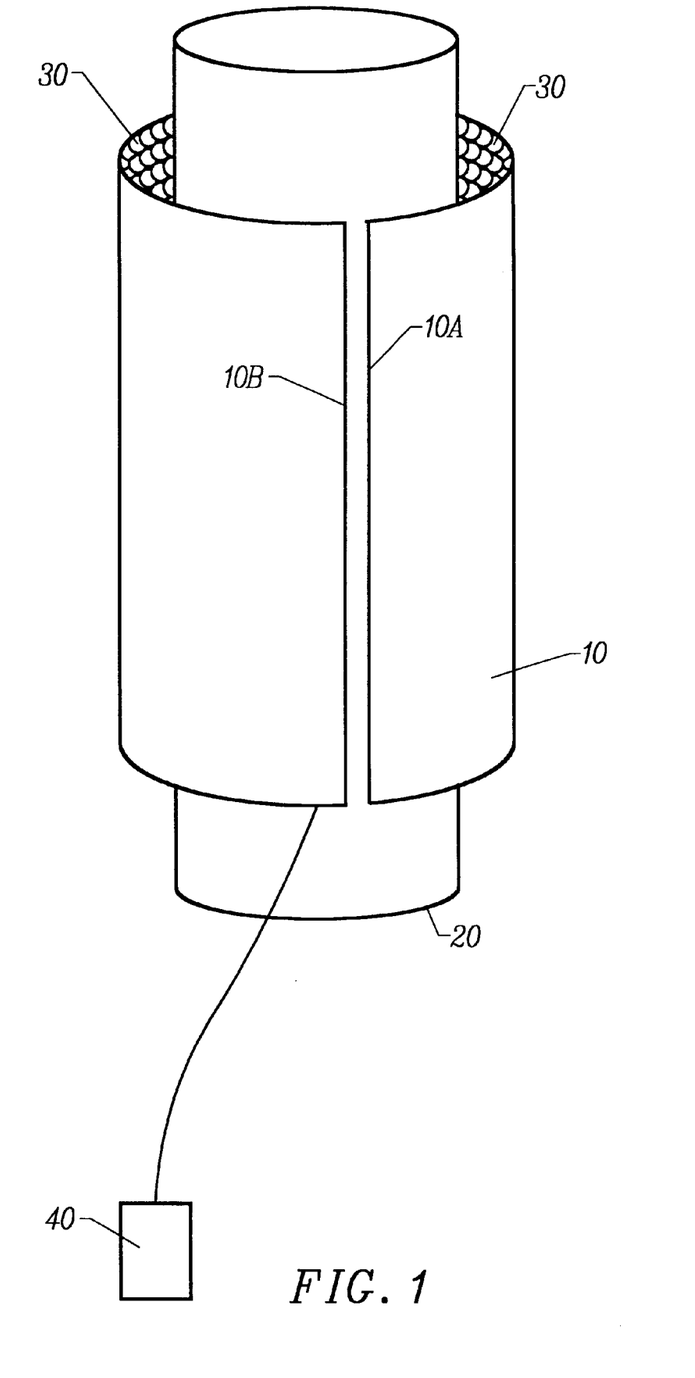
FIG. 1 is a schematic perspective illustration of a pliable light-emitting sheet constructed in accordance with an embodiment of the present invention which acts as a continuous sheetlike light source to provide shadowless lighting of an object.

Referring now to the drawings, wherein like reference numerals designate identical or corresponding parts throughout the several views, and more particularly to FIG. 1 thereof, there is illustrated an embodiment of a pliable light-emitting sheet according to the present invention formed as lighting sheet 10. The lighting sheet 10 is made up of a pliable and supple sheet member, and thus is able to curve around an object 20 that is to receive shadowless lighting from the lighting sheet 10.

The lighting sheet 10 is provided with a plurality of light emitting elements which are attached to a surface of the lighting sheet. In this embodiment, the lighting elements are in the form of light-emitting diodes 30 otherwise known as L.E.D.s. The L.E.D.s are supported on the lighting sheet in the form of a densely arranged matrix of L.E.D.s. When the L.E.D.s are illuminated, the lighting sheet functions as a substantially continuous sheetlike light source.

Each of the light emitting elements are connectable to an electrical source 40. The electrical source 40 may be a main electricity supply or a stored supply such as a battery. The actual nature of the electrical source 40 is not critical, so long as the lighting elements are able to be supplied with an appropriate amount of electricity.

A feature of the present invention is that the sheet member is supple. By way of contrast, lighting elements in the abovementioned prior art U.S. Pat. No. 5,580,163 (Johnson) are held on a flexible membrane that is held taut without the need for the membrane, itself, to flex and curve. In the present invention, the sheet member that supports the lighting elements is, itself, required to flex and be formed, if necessary, in a curved or irregular form or shape. Therefore, the sheet member of the present invention is supple.

The suppleness of the sheet member enables the sheet member to be pliably and curvaceously shaped in order to allow the sheet to conform to a desired disposition, curvature or shape so as to act as a shadowless light source for an object. In this regard, FIGS. 1 and 2A illustrate an embodiment of sheet 10, being used to provide shadowless lighting for a cylindrically-shaped object 20.

A distinct advantage of embodiments of the present invention is that the light-emitting sheet is able to provide shadowless lighting for an irregularly-shaped object, because the sheet member is capable of being formed into an irregular shape in order to substantially conform to the shape of the object. FIG. 2B illustrates an embodiment of a light-emitting sheet that is used to provide shadowless lighting for the wedge shaped cavity 50 in an object 21. The shape of lighting sheet 10 conforms to the wedge-shaped cavity 50 allowing light to be evenly distributed on an interior surface thereof. Such conformation would be either difficult or impossible if the sheet member were not supple, pliable and formable.

The supple sheet member is able to be set permanently in the desired disposition, curvature or shape using a reinforcing agent. In the present embodiment, the reinforcing agent is a fiberglass-reinforced epoxy that is able to be applied to the surface of the sheet member. Once the sheet member is shaped as desired, the reinforcing agent is applied to the surface. In this case, the epoxy resin is applied together with layers of fiberglass, which cures to form a hard backing that provides permanence of form to the sheet member.

Other suitable reinforcing agents may be used to achieve a similar effect, for example a hard lacquer, depending on the strength required. The main function of the reinforcing agent is to lend structural strength to the supple sheet member, and, to this end, any number of material or materials may be applied to the surface.

Figure 2C:
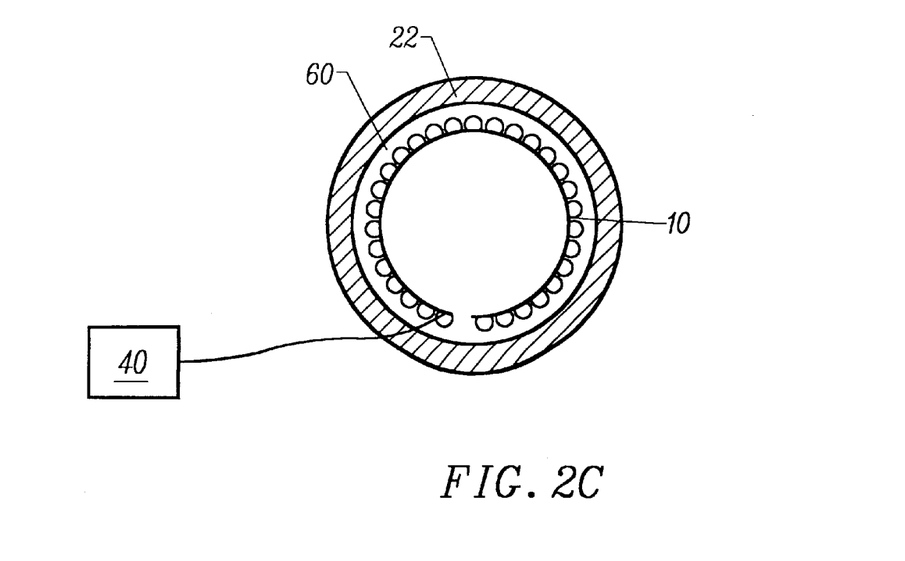
FIG. 2C is a cross-sectional view of the present invention formed to provide shadowless lighting in an interior passageway of an object.
Figure 3:
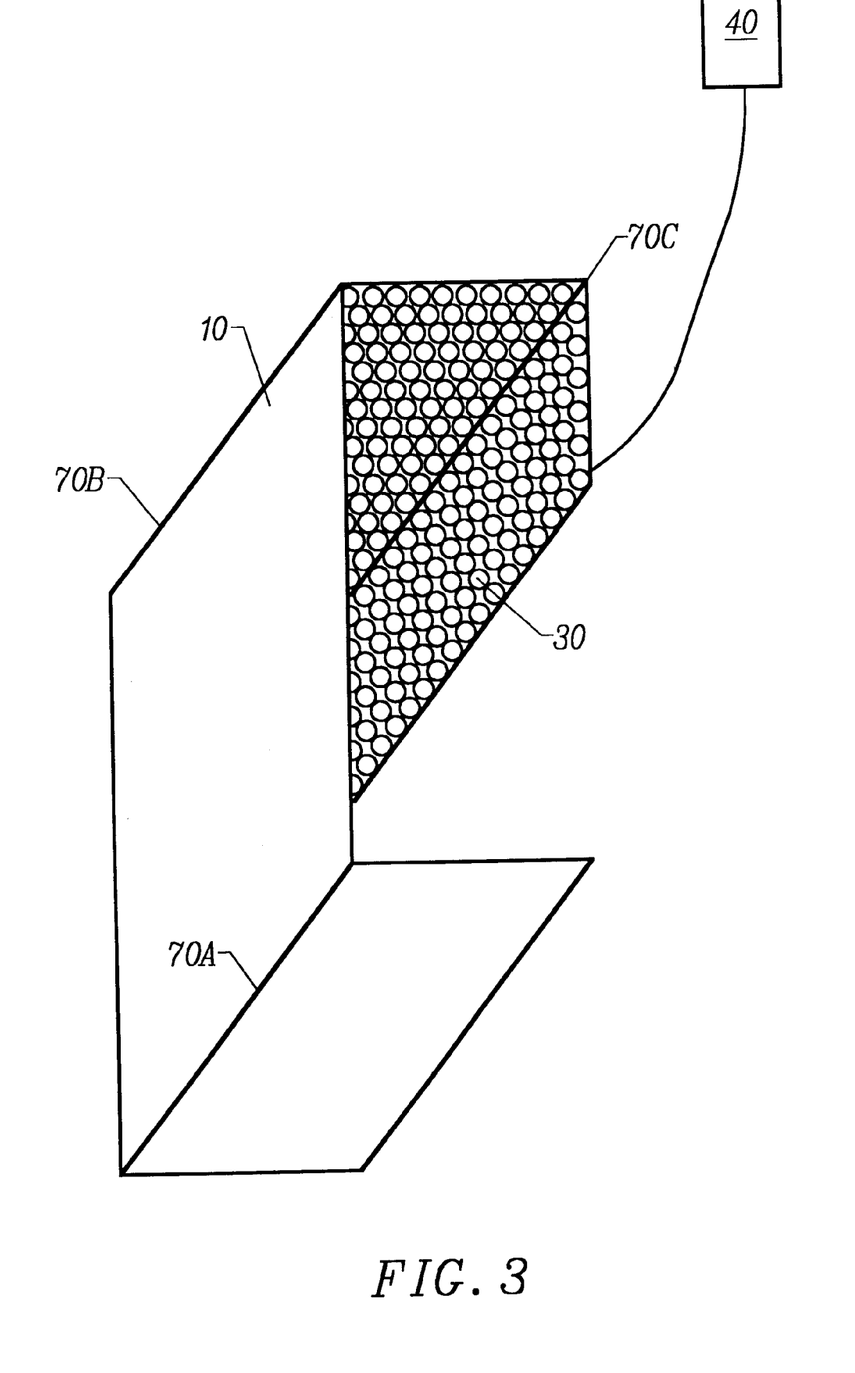
FIG. 3 is a perspective illustration of an embodiment of a pliable light-emitting sheet according to the present invention that has been pliably and curvaceously formed into a shape such that there are bends or creases in the sheet.

FIG. 2C illustrates a further embodiment of the lighting sheet 10 that is used to illuminate an interior surface of a passageway 60 in an object 22. In this case the lighting sheet 10 formed cylindrically with the light-emitting elements emitting light radially outward, thus illuminating the interior surface of passageway 60. As with the above-described embodiments, this configuration allows light to be evenly distributed on the surface to be illuminated.

The invention is particularly suitable in providing lighting for the type of irregular shaped objects that have surface contours that would otherwise create shadows, even when lit by lighting sources that completely surround the object. For example, if the object 21 in FIG. 2B were to be lit by a lighting source that merely surrounds the object completely, but was not able to conform to the surface topography of the object, there may be shadows or regions of uneven illumination in the edges of the crevices.

In extreme cases, the lighting sheet may be curvaceously shaped to such an extent that creases are created in the sheet. Thus, for example in FIG. 3, the lighting sheet 10 has been curvaceously shaped to form a lighting sheet shaped with orthogonal sides and having creases 70A, 70B, and 70C. In this patent specification, this manner of shaping the lighting sheet with creases is still regarded as being a curvaceous shaping of the sheet.

The pliable sheet member is preferably in the form of a pliable and supple printed circuit board (P.C.B.). Each of the L.E.D.s is positioned on the sheet member and connected to an electrical circuit on the P.C.B. of the sheet member. The circuit on the sheet member is connectable to an electrical power supply, so that each of the L.E.D.s is connected in parallel to a common electrical source.

Figure 4:
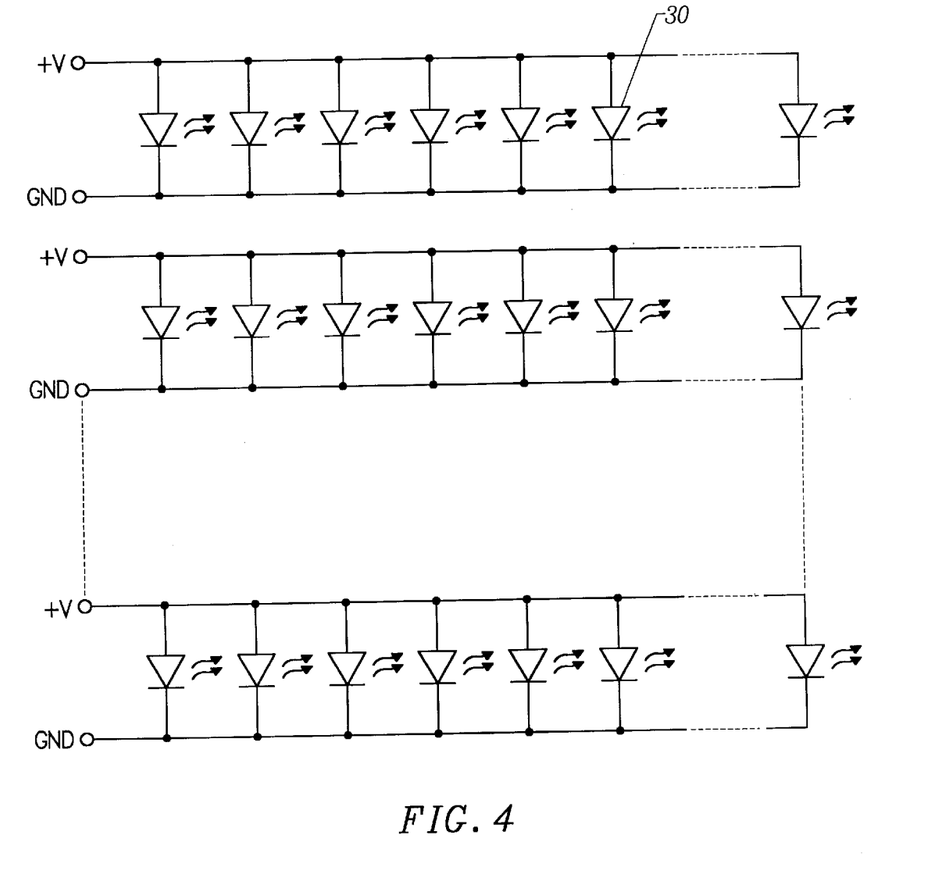
FIG. 4 is a circuit diagram of an embodiment of the pliable light-emitting sheet according to the present invention.
Figure 5:
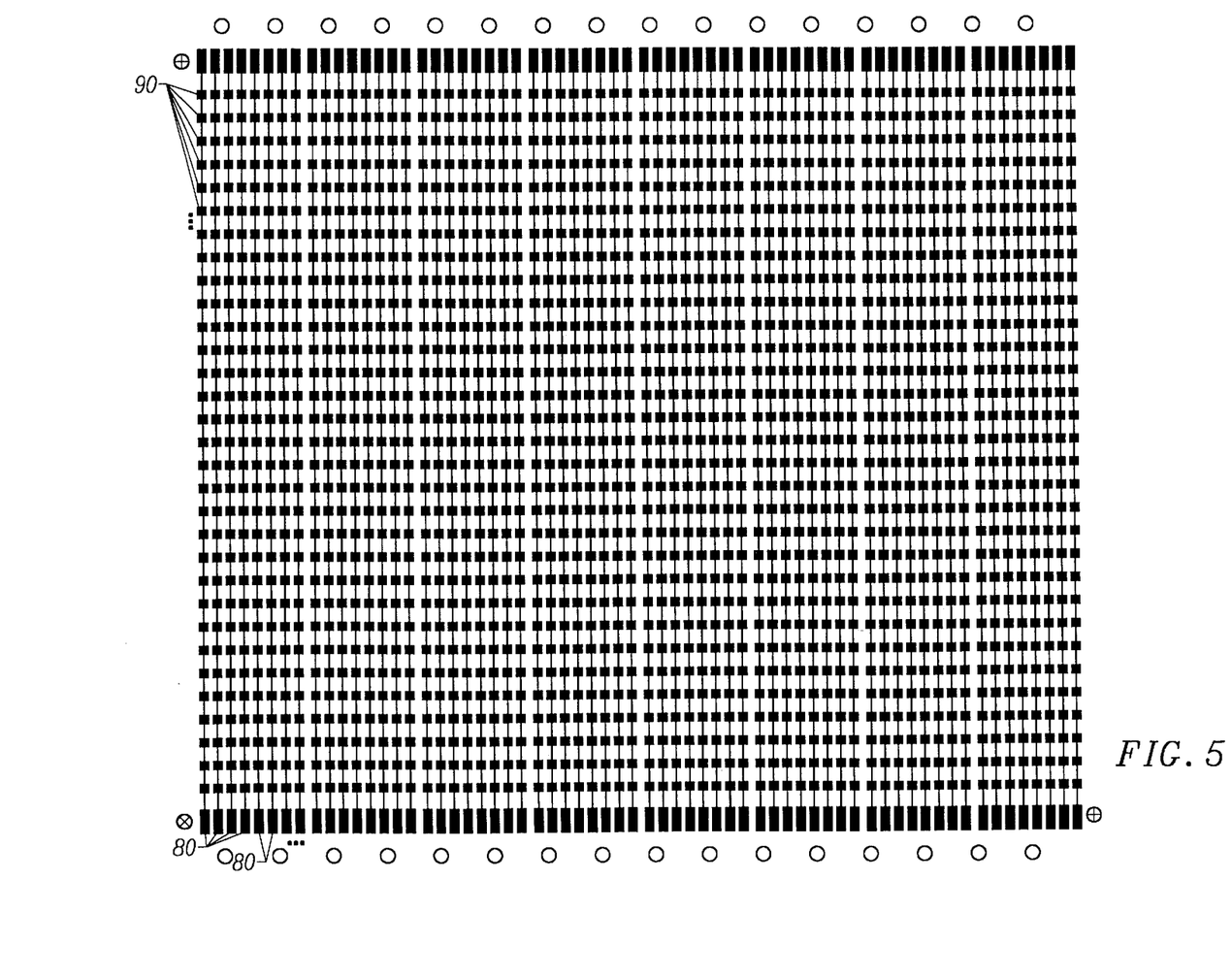
FIG. 5 is an illustration of a flexible P.C.B. solder track of an embodiment of the pliable light-emitting sheet according to the present invention.

An example of a circuit diagram of a number of L.E.D.s connected in parallel is shown in FIG. 4, and a flexible P.C.B. solder track of an embodiment of the pliable light-emitting sheet is shown in FIG. 5. The details of the electronics required for this invention are not complex, and conventional circuit components may be utilized when constructing the invention.

A feature of the invention is in the nature and beneficial use of a pliable and supple sheet member. The actual design of electronics implementing the sheet member can be accomplished in various circuit configurations of which FIG. 5 is one example.

In FIG. 5, plural solder tracks 80 are fitted on a supple sheet. Each solder track has an end 85 for the connection of at least one of voltage or ground, and at least one connection mode 90 for attaching one of the L.E.D.s. In this manner, the L.E.D.s may be connected in parallel as described above. However, other electronic and solder track configurations are also applicable and further electronic configurations are also described herein, but again, the electronic layout of the invention should in no way be limited to these examples.

In the present embodiment, the light emitting elements are each able to emit light at a same level of light intensity. However, it is advantageous for the intensity of light emitted from the plurality of light emitting elements to be adjustable. This is particularly useful when the level of light intensity must be varied, perhaps to allow optimum viewing conditions or when the light must be varied while photographing the object. One way to achieve this would be connection of a regulator (not shown) to one or more of the solder tracks 80.

In other embodiments, the intensity of light emitted from at least one of the light emitting elements is able to be adjusted independently with respect to the rest of the elements. Thus, one or more portions of the light emitting sheet are able to have a higher light output compared with the rest of the sheet. This enables the light intensity to be varied selectively, so that certain portions of the object may be given a higher intensity of lighting. To achieve this, the circuitry of the printed circuit board would have to be varied using circuit technology that allows light intensity of individual L.E.D.s to be varied independently from the light intensity of adjacent L.E.D.s.

The sheet member may be cut to size, depending on the size of the object to be illuminated. The flexible circuit board may be provided with score lines to facilitate breakage or cutting of the circuit board, so that the board may be more easily cut or broken to the desired size and/or shape. In use, parts of the sheet member may also be joined to other parts of the same member. For example, in FIG. 1, ends 10A and 10B of the sheet member 10 may be joined together, so that the entire light-emitting sheet becomes fully cylindrical in shape.

The present invention also includes the ability to create intentional shadows useful in detecting the existence of protuberances on a surface of an object being tested. For instance, if a directional lighting (which is effectively what would happen if certain regions of the light sheet were dimmed or turned off) is shown on a surface with a protuberance, a shadow would result. In quality control procedures, the presence of intentional shadows would be a reassurance that the protuberance was present on the surface as intended.

Figure 6A:
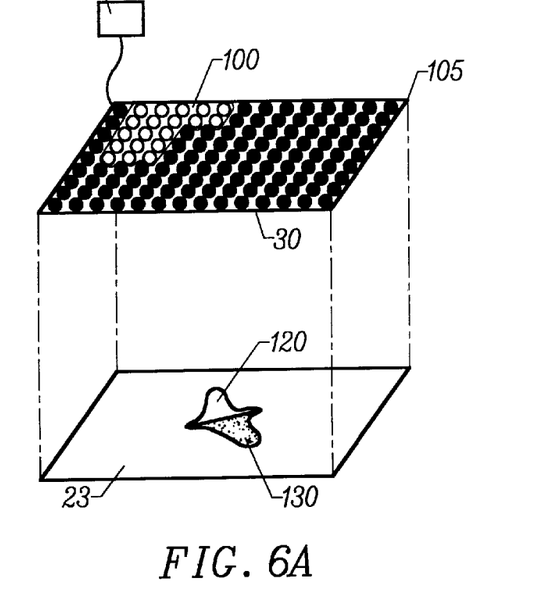
FIG. 6A is a perspective illustration of the present invention wherein lighting elements have been activated in a pattern to intentionally produce a shadow from a feature of an object in a predetermined direction.
Figure 6B:
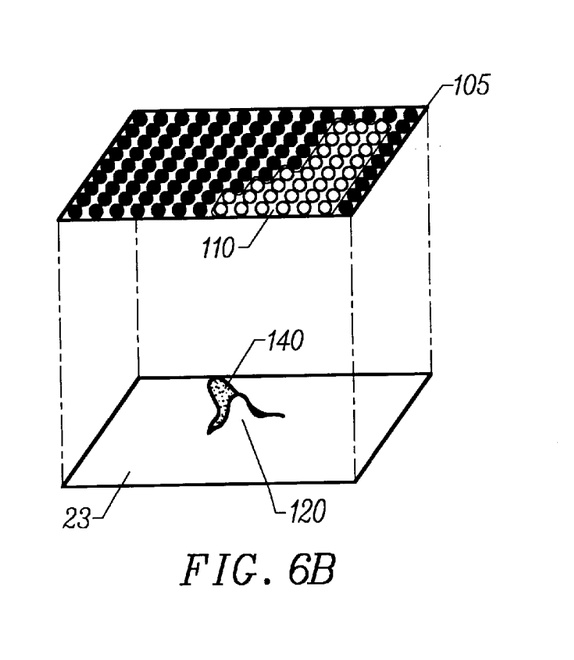
FIG. 6B is a perspective illustration of the present invention wherein lighting elements have been activated in a pattern to produce a shadow from the feature in a second predetermined direction.

FIGS. 6A and 6B illustrate an Object 23 having a protuberance 120 thereon. The diodes 30 of lighting sheet 105 are lit in a predetermined pattern 100 (shaded diodes of diodes 30 are diodes that have been either turned off or had the light intensity thereof varied, and non-shaded diodes of diodes 30 are displaying full light intensity, for example. Many other alternatives are possible, including varying the intensity of all diodes 30 on the lighting sheet 105) such that directional lighting is provided to cast a shadow 130 (FIG. 6A) from the protuberance 120 in a first predetermined direction).

In FIG. 6B, a second predetermined pattern 110 of lit or varied intensity diodes on the lighting sheet 105 provides directional lighting toward the protuberance 120. The directional lighting casts shadow 140 from the protuberance 120 in a second predetermined direction.

Lighting patterns 100 and 110 can be created by asserting individual control over the lighting of diodes 30 through individual electrical connections and either manual switches or computer controlled activation of those diodes, or may be controlled via manual switches or computer activated control of sets of the diodes via the soddered tracks 80. Individual control of the LEDs could be performed by individually controlling electrical characteristics provided to individual of connection nodes 90 on which the LEDs are attached. Again, such control could be provided via manual switches and/or computer activation. Other methods of controlling individual lighting and/or sets or groups of LED lighting to either be turned off or dimmed would also apply within the scope of the present invention.

In the description of embodiments of the invention, the word "sheet" is not to be construed to imply any limitations on the shape or dimensions of the sheet. A sheet merely is required to be a thin, pliable member, normally, but not required, to be of substantial planar dimension. Typically, the sheet would be orthogonal in shape, having straight and perpendicular edges, but this is by no means the only possible shape. The sheet may be made in a variety of shapes and dimensions, for example, circular or even irregular-shaped sheets.

Obviously, numerous modifications and variations of the present invention are possible in light of the above teachings. It is therefore to be understood that within the scope of the appended claims, the invention may be practiced otherwise than as specifically described herein.

What is claimed is:

1. A shadowless light source which illuminates an object, said shadowless light source comprising:
    a continuous sheet like light source, comprising,
        a pliable and supple sheet member having a plurality of light emitting elements attached continuously and throughout said sheet member in an x-y plane defined by said sheet member, and
        plural electrical paths connecting each of said light emitting elements to an electrical source;
    wherein said supple sheet member is capable of being pliably and curvaceously shaped in order to allow said sheet to conform to at least one of a predetermined disposition, curvature, and shape to provide shadowless lighting on said object.

2. The shadowless light source according to claim 1, wherein:
    each of said plurality of light emitting elements is a light emitting diode,
    and said plurality of light-emitting elements are supported on said sheet member as a densely arranged matrix of said diodes.

3. The shadowless light source according to claim 2, wherein said object is irregularly shaped and said sheet member is capable of being formed into an irregular shape in order to substantially conform to the irregular shape of said object to provide shadowless lighting on said irregularly-shaped object.

4. The shadowless light source according to claim 3, wherein said pliable and supple sheet member is constructed of a pliable and supple printed circuit board.

5. The shadowless light source according to claim 4, wherein each of said diodes is connected in parallel to said electrical source.

6. The shadowless light source according to claim 1, wherein said supple sheet member is able to be set permanently in said at least one of a predetermined disposition, curvature, and shape using a reinforcing agent.

7. The shadowless light source according to claim 6, wherein said reinforcing agent is a fiberglass-reinforced epoxy that is applied to a surface of said sheet member.

8. The shadowless light source according to claim 1, further comprising:
    an adjustment device attached to at least one of said plurality of light-emitting elements, said adjustment device configured to adjust an intensity of light emitted from the attached light-emitting elements.

9. The shadowless light source according to claim 8, wherein said adjustment device is further configured to adjust an intensity of light emitted from at least one of the attached light-emitting elements independently with respect to a light intensity of other of said plurality of light emitting elements.

10. A method of using a shadowless light source to shadowlessly illuminate an object, said shadowless light source comprising, a continuous sheet like light source having a pliable and supple sheet member, and a plurality of light emitting elements attached continuously and throughout said sheet member, comprising the steps of:
    providing said shadowless light source;
    pliably and curvaceously forming said pliable and supple sheet member in at least one of a predetermined disposition, curvature, and shape matching said object; and
    illuminating said object with said light emitting elements in order to enable said light emitting elements to provide shadowless lighting on said object.

11. The method according to claim 10, wherein:
    said light-emitting elements are light-emitting diodes attached to said sheet member as a densely arranged matrix of said diodes.

12. The method according to claim 11, wherein:
    said object is an irregularly shaped object; and
    said step of pliably and curvaceously forming comprises the step of forming said sheet member into an irregular shape in order to substantially conform to said irregularly-shaped object so as to act as a shadowless light source for said irregularly-shaped object.

13. The method according to claim 12, wherein said pliable sheet member is constructed from a pliable and supple printed circuit board.

14. The method according to claim 11, wherein each of said diodes are connected in parallel to an electrical source.

15. The method according to claim 10, further comprising the step of setting said pliable and supple sheet member permanently in said at least one of a predetermined disposition, curvature, and shape.

16. The method according to claim 15, wherein said step of setting includes the substep of applying a reinforcing agent to said pliable and supple sheet member.

17. The method according to claim 16, wherein said substep of applying includes the substep of utilizing a fiberglass reinforced epoxy as said reinforcing agent.

18. The method according to claim 15, wherein said step of setting includes the substep of applying a reinforcing agent to a surface of said pliable and supple sheet member.

19. The method according to claim 10, further comprising the step of adjusting an intensity of light emitted from said plurality of light emitting elements.

20. The method according to claim 10, further comprising the step of adjusting an intensity of light emitted from at least one of said plurality of light emitting elements independently with respect to a light intensity of other of said plurality of light emitting elements.

21. The method according to claim 20, wherein said step of adjusting comprises the substep of adjusting selected of said light emitting elements by one of increasing intensity, decreasing intensity, and turning off light emitted therefrom in order to provide directional lighting.

22. A directional lighting device for inspection of objects, comprising:
    a continuous sheet like light source, comprising,
        a pliable and supple sheet member having a plurality of light emitting elements attached continuously and throughout said sheet member in an x-y plane defined by said sheet member;

electrical paths each connected to at least one of said light-emitting elements; and a connection device configured to connect selected of said light emitting elements to an electrical source via selected of said electrical paths to provide said directional lighting for inspection.

23. The light-emitting sheet according to claim 22, further comprising a programmable power control device configured to provide electrical power to said light-emitting elements, and selectively power individual of said light emitting elements at a range of power settings, thereby individually setting an amount of light emitted from each light emitting element.

* * * * *